United States Patent [19]

Makino et al.

[11] Patent Number: 5,182,274
[45] Date of Patent: Jan. 26, 1993

[54] STABILIZED AQUEOUS PREPARATION OF ACTIVE FORM OF VITAMIN $D_3$

[75] Inventors: Yuji Makino; Hideo Matugi; Yoshiki Suzuki, all of Hino, Japan

[73] Assignee: Teijin Limited, Osaka, Japan

[21] Appl. No.: 490,637

[22] PCT Filed: Sep. 21, 1989

[86] PCT No.: PCT/JP89/00959
§ 371 Date: May 25, 1990
§ 102(e) Date: May 25, 1990

[87] PCT Pub. No.: WO90/03173
PCT Pub. Date: Apr. 5, 1990

[30] Foreign Application Priority Data

Sep. 26, 1988 [JP] Japan .................................. 63-238971

[51] Int. Cl.$^5$ .............................................. A61K 31/59
[52] U.S. Cl. ...................................................... 514/167
[58] Field of Search ......................................... 514/167

[56] References Cited

U.S. PATENT DOCUMENTS

| 4,308,264 | 12/1981 | Conway et al. | 514/167 |
| 4,729,895 | 3/1988 | Makino et al. | 424/465 |
| 4,836,957 | 6/1989 | Nemoto et al. | 260/397.2 |

OTHER PUBLICATIONS

Chemical Abstracts 97:163329f (1982).
Chemical Abstracts 96:57766r (1982).
Chemical Abstracts 100:91354n (1984).
Chemical Abstracts 95:121145w (1981).
Chemical Abstracts 92:64750b (1980).
Merck Index, 9th ed., 1976 2307.

Primary Examiner—Leonard Schenkman
Attorney, Agent, or Firm—Sughrue, Mion, Zinn, Macpeak & Seas

[57] ABSTRACT

An aqueous preparation of active form of vitamin $D_3$ which is solubilized with a nonionic surface active agent and stabilized with a combination of a specific chelating agent such as citric acid with an antioxidant. Stabilized oral and parenteral preparations of active form of vitamin $D_3$ can be provided.

7 Claims, No Drawings

STABILIZED AQUEOUS PREPARATION OF ACTIVE FORM OF VITAMIN $D_3$

THE FIELD OF THE ART

The present invention relates to a stabilized aqueous preparation of active form of vitamin $D_3$.

Particularly, the present invention relates to an aqueous preparation of active form of vitamin $D_3$ which is solubilized into water using a nonionic surface active agent, and stabilized with a combination of at least one selected from the group consisting of citric acid, tartaric acid and their metal salts with an antioxidant.

THE BACKGROUND OF THE INVENTION

It has been clarified that active form of vitamin $D_3$, typified by $1\alpha$-hydroxycholecalciferol, $1\alpha,25$-dihydroxychole-calciferol or $1\alpha,24$-dihydroxycholecalciferol, is absorbed in the body, binds to the receptors distributing in intestinal tracts, kidney, parathyroid gland and bone tissues to develop its pharmacological actions such as Ca absorption from intestinal tracts, increase of serum Ca level, secretory inhibition of parathyroid hormone or bone formation. Thus, the active form of vitamin $D_3$ is clinically applied to a variety of symptoms (hypocalcemia, tetany, bone ache, bone lesion, and so on) accompanied by dysbolism of vitamin D in chronic renal failure, hypoparathyroidism, vitamin D resistant rickets, and osteomalacia, as well as for treatment of osteoporosis.

These active forms of vitamin $D_3$ are chemically unstable and cannot be clinically applied without establishment of production of stabilized preparations. And many methods have been proposed.

For example, Japanese patent specification No. 57-45415 (1982), Japanese patent specification No.61-41351 (1986), Japanese patent specification No. 62-51948 (1987), Japanese patent specification No. 58-206533 (1983), U.S. Pat No. 4,729,895 (Japanese patent specification laid-open No. 59-155309 (1984) disclosed the stabilization processes for oral preparations, and the soft capsules and tablets prepared from $1\alpha$-hydroxycholcalciferol, $1\alpha,25$-dihydroxycholecalciferol or $1\alpha,24$-dihydroxycholecalciferol by the disclosed techniques have been practically used in the clinical fields.

These techniques relates, however, to the stabilization of only non-aqueous liquid preparations or solid preparations.

Meanwhile, aqueous preparations, particularly stabilized preparations of active form of vitamin $D_3$ have been strongly desired clinically for the intravenous administration to chronic renal failure or for continuous application to premature babies and infants with convenience of application enhanced and side-effects decreased.

As for such stabilization of aqueous preparation, U.S. Pat. No. 4,308,264 (Japanese patent specification 61-44845 (1986)) disclosed a method for stabilizing $1\alpha,25$-dihydroxycholecalciferol in injection preparations and oral liquid preparations. Japanese patent specification laid-open No. 62-17 (1987) described a method for stabilizing an active form of vitamin $D_3$ in aqueous solution by admixing some kinds of amino acids.

The present inventors have found, however, in the course of their study of the production of aqueous preparations of active forms of vitamin $D_3$, that these conventional arts include great problems from a practical point of view.

In other words, the method according to U.S. Pat. No. 4,308,264 has following 2 problems:

First, the method described in the patent is effective for stabilization of 1,25-dihydroxycholecalciferol, to be sure, but the stabilization effect is limited to the conditions in the presence of inert atmosphere, as the specification told it.

But, it should be recognized that the actual conditions for the aqueous preparations to be given clinically are not always kept as the preparation has been provided in an inert atmosphere, in other words, actual administration is not limited only to the case where a unit dosage form which has been prepared in an inert atmosphere is given only in intravenous or oral bolus, namely the whole amount of the unit dose is given in single application. For example, even in intravenous administration, when it is given together with other drugs, the preparation is given intravenously by continuous infusion in more cases than by bolus injection. And in such a case, the preparation of active form of vitamin $D_3$ which has been provided in an inert atmosphere will be mixed with large amounts of other aqueous preparations which have not been in an inert atmosphere. In another case where it is orally given to infants as an oral aqueous preparation, it is more simple and economical that a part of a large volume of the aqueous preparation is given in portions than the unit dose forms which have been provided in an inert atmosphere are given every time of administration. In this case, once the preparation has been employed, it is impossible to maintain the inert atmosphere.

The inventors of the present invention actually found that this stabilization method has serious problems under the conditions where the inert atmosphere has been broken or the inert atmosphere has not been taken into consideration. In other words, under the condition where the atmosphere was not inert, namely contained oxygen, the decomposition of the active form of vitamin $D_3$ was noticed in the method and the decomposition rate was found to be so large as to become an issue from a practical point of view.

Accordingly, an aqueous preparation of active form of vitamin $D_3$ which is stable even in the presence of oxygen is required.

Secondly, when an aqueous preparation of $1\alpha,25$-dihydroxycholecarciferol was provided by insolubilizing the compound from water at a pH ranging from 6.4 to 7.8 with a nonionic surface active agent and stabilizing it with a combination of a metal salt of ascorbic acid and disodium edetate to provide an aqueous preparation, and the storage test of the preparation was conducted in ampules, it was found to be susceptible to heat and cause such a level of yellowing as it may happen in high possibility in the usual distribution process of medical and pharmaceutical products.

Accordingly, an aqueous preparation of $1\alpha25$-dihydroxycholecalciferol resistant to discoloration or an aqueous preparation of active form of vitamin $D_3$ resistant to discoloration is desired.

The present inventors have made intensive effort to resolve these problems and found that an aqueous preparation of active form of vitamin $D_3$ which is resistant to discoloration and stable even in the presence of oxygen can be produced by solubilizing the active form of vitamin $D_3$ with a nonionic surface active agent and adding a combination of at least one of chelating agents selected from the group consisting of citric acid, tartaric acid and their metal salts with an antioxidant and reached the present invention.

It has been generally known that stabilized aqueous preparations of fat-soluble vitamins, for example, vitamin A, vitamin D, vitamin E or vitamin K are produced by solubilizing the fat-soluble vitamin using a surface active agent, and admixing an antioxidant and a chelating agent, when necessary, further an isotonic agent, a preservative, a buffering agent and so on. These arts should be referred to E. DeRitter, J. Pharm. Sci., 71, 1074 (1982), U.S. Pat. Nos. 3,070,499 and 3,384,545. And, as conventionally known chelating agents, are cited disodium edetate, citric acid and its metal salts, tartaric acid or its metal salts, a variety of amino acids, phosphoric acid and so on [cf. "Chemical Stability of Pharmaceuticals" edited by K. A. Conners et al, published from John Wiley μ Sons (1986)].

In fact, disodium edetate was used as a chelating agent in the U.S. Pat. No. 4,308,264, while amino acids were used in the Japanese patent specification of laid-open No. 62-17 (1987), although there was no description of the term, chelating agent. But, there has been no general rank of these conventionally known chelating agents in their stabilization effect on the pharmaceuticals, much less the mutual comparison between them have not been investigated about their stabilization effect on aqueous preparations of active form of vitamin $D_3$. Moreover, attention should be paid to that the U.S. Pat No. 4,308,264 actually confirmed the effect of only disodium edetate as a chelating agent, but not mention at all other chelating agents.

Therefore, it would be understood that the following findings (they will be illustrated in the examples) by the present inventors are unpredictable at all from the hitherto accumulated knowledge of stabilization of unstable compounds in aqueous preparations, particularly from the known facts on the stabilization process for active form of vitamin $D_3$ in aqueous preparations described in U.S. Pat. No. 4,308,264 and Japanese patent specification Laid-open No. 62-17 (1987):

(1) the aqueous preparations of active form of vitamin $D_3$ in which disodium edetate is used as a chelating agent is susceptible to yellowing under heating, but the yellowing is markedly suppressed by using at least one selected from the group consisting of citric acid, tartaric acid and their metal salts, (2) disodium edetate is effective for stabilizing the active form of vitamin $D_3$ in an aqueous preparation under an inert atmosphere, while, on the contrary, the chelating agent loses its stabilization effect, and rather manifests adverse effect in the presence of oxygen.

(3) chelating agents other than disodium edetate, particularly citric acid and tartaric acid, namely hydroxycarboxylic acids, and their metal salts are effective for stabilizing the active form of vitamin $D_3$ not only in the absence of oxygen, but also in the presence of oxygen.

In the U.S. Pat. No. 4308,264, a metal salt of ascorbic acid is used to stabilize active form of vitamin $D_3$, but it is unnecessary for the antioxidant to be limited to metal salt of ascorbic acid in the present invention and other effective antioxidants may be employed characteristically.

In other words, the oxygen concentration must be highly lowered in the U.S. Pat. No. 4,308,264, because disodium edetate is employed (the coexistence of disodium edetate and oxygen exerts adverse effect on the active form of vitamin $D_3$), and sodium ascorbate must be used, which has high potency of absorbing dissolved oxygen. On the contrary, it is unnecessary for the present invention to lower the dissolved oxygen markedly, thus sodium ascorbate is not always required, and tocopherol, butylhydroxytolutene, butylhydroxyanisole, propyl gallate or nordihydroguaiaretic acid, having antioxidant power, may be solubilized with a nonionic surface active agent.

DISCLOSURE OF THE INVENTION

Thus, the present invention is an aqueous preparation of active form of vitamin $D_3$ which is solubilized in water with a nonionic surface active agent and stabilized with a combination of at least one chelating agent selected from citric acid, tartaric acid and their metal salts with an antioxidant.

BEST EMBODIMENT FOR THE PRESENT INVENTION

As a nonionic surface active agent used in the present invention, is cited suitably polyoxyethylene sorbitan fatty acid esters, polyoxyethylene hardened castor oil derivatives, sorbitan fatty acid esters, glycerol fatty acid esters, propylene glycol fatty acid esters, polyethylene glycol fatty acid esters, polyoxyethylene alkyl ethers, and sucrose fatty acid esters. One example of polyoxyethylene hardened caster oil derivatives is HCO-60 ® (produced by Nikko chemicals Co.). The polyoxyethylene sorbitan fatty acid is, for example, polyoxyethylene (20) sorbitan monooleate (Tween 80 ®).

The chelating agent used in the present invention is at least one selected from the group consisting of citric acid, tartaric acid, and their metal salts. The citric acid may be also anhydride or monohydrate. The tartaric acid may be D-isomer, L-isomer or DL racemic isomer. The metal salts of citric acid and tartaric acid may be sodium, potassium and other metal salts and the sodium salts are particularly preferred.

The antioxidant used in the present invention is a metal salt of ascorbic acid as a water-soluble antioxidant or tocopherol, butylhydroxytoluene, butylhydroxyanisole, propyl gallate, nordihyroguaiaretic acid as a fat-soluble antioxidant. The water-soluble antioxidant is used by dissolving it directly in the aqueous preparation, while the fat-soluble antioxidant is employed by solubilizing it with a nonionic surface active agent. Sodium ascorbate is preferred as a metal salt of ascorbic acid.

The active form of vitamin $D_3$ used in the present invention is, for example, active forms of vitamin $D_3$ bearing a hydroxyl group in the 1α-position, such as 1α-hydroxycholecalciferol (1α-OH-$D_3$), 1α,25-dihydroxycholecalciferol [1α,25-(OH)$_2D_3$], 1α,24-dihydroxycholecalciferol [1α,24-(OH)$_2D_3$], 1α,24,25-trihydroxycholecalciferol [1α,24,25-(OH)$_3D_3$], 1α-hydroxy-24-oxocholecalciferol, 1α,25-dihydroxy-24-oxocholecalciferol, 1α25-dihydroxycholecalciferol-26,23-lactone, 1α,25-dihydroxycholecalciferol-26,23-peroxylactone, 26,26,26,27,27,27-hexafluoro-1α,25-dihydroxycholecalciferol, or active forms of vitamin $D_3$ bearing no hydroxyl group on the 1α-position such as 25-hydroxycholecalciferol (25-OH-$D_3$), 24-hydroxycholecalciferol (24-OH-$D_3$), 24-oxocholecalciferol, 24,25-dihydroxycholecalciferol [24,25-(OH)$_2$-$D_3$], 25-hydroxy-24-oxocholecalciferol, 25-hydroxycholecalciferol-26,23-lactone, or 25-hydroxycholecalciferol-26,23-peroxylactone.

The chelating agent is usually used 100 to 10,000 parts by weight per 1 part by weight of active form of vitamin $D_3$, and preferably 500 to 2,000 parts by weight in the present invention.

The amount of the antioxidant used in the present invention is usually 500 to 20,000 parts by weight per 1 part of active form of vitamin $D_3$, preferably 1,000 to 15,000 parts by weight.

The nonionic surface active agent is usually used 300 to 500,000 parts by weight per 1 part of active form of vitamin $D_3$, preferably 1,000 to 10,000 parts by weight.

An aqueous preparation of active form of vitamin $D_3$ stabilized even in the presence of oxygen is provided according to the present invention. It is clear, from the object of the present invention, that the preparation according to the present invention is not always necessary to exclude oxygen in the administration as well as in the production and storage, but oxygen may be excluded, when needed. When oxygen is excluded, it is preferred that the oxygen dissolved in the liquid is removed and the oxygen in the vessels is also excluded. In order to exclude oxygen effectively, an inert gas such as nitrogen or argon is thoroughly passed through the liquid, and the gas in the vessel is replaced with an inert gas, when the preparation is sealed in a vessel.

Stabilized aqueous preparations of active form of vitamin $D_3$ are provided according to the present invention and the resultant liquid preparations are further prescribed into oral or parenteral preparations.

As an oral preparation, they are prescribed into solutions or syrups. In this case, flavoring agents and corrigents may be added. As a parenteral preparation, they are prescribed into intravenous injection solutions, intramuscular injection solutions, eye drops, etc. In this case, isotonic agents, preservatives, buffers, analgesic agents and other additives may be added. As a preservative, are cited p-hydroxybenzoic acid esters, chlorobutanol, benzalkonium chloride, thimerosal, etc.

The detailed procedures of the aqueous preparation production will be illustrated in the following:

An active form of vitamin $D_3$ is dissolved in a nonionic surface active agent. This operation is preferably conducted in an inert atmosphere. The nonionic surface active agent which is solid at ambient temperature should be heated, until it becomes liquid. An active form of vitamin $D_3$ is added to the liquid or liquefied surface active agent and dissolved by stirring. In another procedure, the active form of vitamin $D_3$ is dissolved in a small amount of ethanol and the solution is added to the surface active agent under stirring. Then, the solution of active form of vitamin $D_3$ in a nonionic surface active agent is added to the distilled water for injection which has been boiled beforehand, simultaneously, chelating agents, antioxidants, and desired isotonic agent, preservative, buffer, analgesic agents are also admixed, then they are dissolved as being stirred under an inert gas atmosphere. After the distilled water for injection is adjusted to the final volume and confirmed, the solution is sterilely filtered in an inert gas atmosphere and a desired amount of the solution is placed in a sterilized and dried ampule. Before sealing, the gas in the head space of the ampule is replaced with a filtered (germ-free) inert gas whereby the aqueous preparation of active form of vitamin $D_3$ is prepared.

The present invention will be illustrated in more detail by the following examples:

EXAMPLE 1

A sterilized ampule of an indicated capacity of 1.25 ml/unit was charged with a sterilized and stabilized aqueous preparation of 1α,24-dihydroxycholecalciferol, having the following formulation:

| Components | amounts/ml |
|---|---|
| 1α,24-hydroxycholecalciferol | 10 μg |
| Tween 802 | 4.0 mg |
| sodium chloride | 1.5 mg |
| sodium ascorbate | 10.0 mg |
| disodium hydrogen phosphate, anhydride | 7.6 mg |
| sodium dihydrogen phosphate, dihydrate | 2.0 mg |
| trisodium citrate, dihydrate | 1.0 mg |
| nitrogen | an appropriate amount |
| distilled water for injection | an appropriate amount |

The aqueous preparation was prepared by the following procedures:

Tween 80 (Nikko Chemicals) 40 grams were heated at 50° C. under a nitrogen atmosphere. After the Tween 20 became liquid, 105 mg of 1α,24-dihydroxycholecalciferol was added, they were continuously stirred under a nitrogen atmosphere, till a homogeneous solution was formed, then cooled down to room temperature.

Meanwhile, about 11 liters of distilled water for injection was heated up to 100° C., boiled for 20 minutes, then cooled down to room temperature under a nitrogen atmosphere. To 10 liters of the cool distilled water, were added 15 grams of sodium chloride, 100 g of sodium ascorbate, 76 g of anhydrous disodium hydrogen phosphate, 20 g of sodium dihydrogen phosphate dihydrate, trisodium citrate dihydrate, and 40 g of the above-stated solution of 1α,24-dihydroxycholecalciferol in Tween 20. They were gradually stirred under a nitrogen atmosphere to give a homogeneous solution. Then, the solution was sterilely filtered in a nitrogen atmosphere, charged in sterilized ampules, the gas in the ampule head was replaced with a filtered (germ-free) nitrogen gas, the ampules were sealed to give an aqueous preparation ampule for intravenous injection.

The aqueous injection preparation of 1α,24-dihydroxycholecalciferol (Example 1) was stored under the conditions described in Table 1 to examine the stability of 1α,24-dihydroxycholecalciferol and the discoloration of the injection preparation (called Experiment A hereinafter). In the meantime, an ampule of the aqueous injection preparation was opened, 1 ml of the content was admixed to 200 ml of physiological saline solution to examine the stability of 1α,24-dihydroxycholecalciferol after 1 hour, 2 hours, and 1 day, as well as the discoloration of the preparation after 1 day (called Experiment B).

Further, disodium edetate was used instead of trisodium citrate dihydrate in Example 1 to provide an aqueous injection preparation in the quite same way (Comparison 1) and another aqueous injection preparation was prepared in the quite same was as in Example 1, except that trisodium citrate dihydrate was removed (Comparison 2) and they were subjected to Experiments A and B, respectively.

The results of Experiments A and B are given in Table 1 and Table 2, respectively.

TABLE 1

Results of Experiment A 1) residual 1,24-dihydroxycholecalciferol (%)

TABLE 1-continued

Results of Experiment A 1) appearance

| | Storage conditions | | | |
|---|---|---|---|---|
| | at 60° C. | | | at 40° C. |
| Preparations | 1 week | 2 week | 4 week | 3 months |
| Example 1 | 90 | 91 | 90 | 96 |
| Comparison 1 | 91 | 92 | 90 | 95 |
| Comparison 2 | 90 | 88 | 87 | 92 |

2) discoloration of the injection preparation

| | at 60° C. | | | at 40° C. |
|---|---|---|---|---|
| Preparation | 1 week | 2 week | 4 week | 3 months |
| Example 1 | No change | a little yellowish | pale yellow | no change |
| Comparison 1 | a little yellowish | pale yellow | dark yellow | pale yellow |
| Comparison 2 | a little yellowish | pale yellow | dark yellow | pale yellow |

2) optical density (OD) at 400 millimicron wavelength

| | at 60° C. | | | at 40° C. |
|---|---|---|---|---|
| Preparations | 1 week | 2 week | 4 week | 3 months |
| Example 1 | 0.005 | 0.150 | 0.233 | 0.005 |
| Comparison 1 | 0.005 | 0.570 | 0.793 | 0.101 |
| Comparison 2 | 0.004 | 0.495 | 0.699 | 0.088 |

TABLE 2

Results of Experiment B
Residual 1,24-dihydroxycholecalciferol (%)

| | after addition to physiological saline solution (containing $O_2$) | | | discoloration |
|---|---|---|---|---|
| Preparation | 1 hour | 2 hours | 1 day | after 1 day |
| Example 1 | 100 | 98 | 97 | almost no change |
| Comparison 1 | 88 | 79 | 59 | slightly yellowish |
| Comparison 2 | 91 | 90 | 88 | slightly yellowish |

As shown in Table 1 and Table 2, the aqueous preparation of 1α,24-dihydroxycholecalciferol in Example 1 according to the present invention was stable both under oxygen-excluded and oxygen-containing conditions and scarcely caused discoloration, while the preparation of comparison 1 in which disodium edetate was used as a chelating agent revealed marked discoloration under oxygen-excluded conditions, although it showed the same level of stability as that in Example 1, but it was markedly unstable compared with Example 1 under oxygen-containing conditions. In addition, it was found to be more unstable than the preparation not containing a chelating agent (comparison 2).

EXAMPLE 2

The experiments described in Example 1 (Experiment A and Experiment B) were repeated on the aqueous preparations 1α,24-dihydroxycholecalciferol which was prepared as in Example 1 according to the present invention except disodium D-tartarate was used instead of trisodium citrate dihydrate (Example 2) and on another aqueous preparation in which glycine was used (Comparison 3). The results are shown in Table 3 and Table 4.

TABLE 3

Results of Experiment A
Residual 1,24-dihydroxycholecalciferol (%)

| | Storage conditions at 60° C. | | |
|---|---|---|---|
| Preparations | 1 week | 2 weeks | 4 weeks |
| Example 2 | 90 | 92 | 91 |
| Comparison 3 | 90 | 86 | 85 |

TABLE 4

Results of Experiment B
Residual 1α,24-dihydroxycholecalciferol (%)

| | Storage conditions After addition to physiological saline solution (containing oxygen) | | |
|---|---|---|---|
| Preparations | 1 hour | 2 hours | 4 hours |
| Example 2 | 99 | 100 | 98 |
| Comparison 3 | 88 | 86 | 85 |

EXAMPLES 3 THROUGH 5

An oral aqueous preparation of 1α-hydroxycholecalciferol was prepared, having the following composition:

| Components | amounts/ml |
|---|---|
| 1α,24-dihydroxycholecalciferol | 1.0 μg |
| HCO-60 ® | 10.0 mg |
| sodium chloride | 1.5 mg |
| tocopherol | 10.0 μg |
| disodium hydrogen phosphate anhydride | 7.6 mg |
| sodium dihydrogen phosphate dihydrate | 2.0 mg |
| trisodium citrate dihydrate | 1.0 mg |
| purified water | an appropriate amount |

The aqueous preparation was prepared as follows:

Forty grams of HCO-60 ® (Nikko Chemicals) was heated at 60° C. When the HCO-60 became liquid, 10.5 mg of 1α-hydroxycholecalciferol was added, they were stirred, until a homogeneous solution was formed, and cooled down to room temperature. Meanwhile, 15 g of sodium chloride, 76 g of disodium hydrogen phosphate anhydride, and 10 g of trisodium citrate dihydrate were dissolved in 10 liters of purified water. Additionally, 60 g of HCO-60 ® was heated at 60° C., 0.1 g of tocopherol was added to the liquid HCO-60 ® to form a homogeneous solution, which was then cooled down to room temperature. These two HCO-60 ® solutions were added in order to the aqueous solution stated above, they were gradually stirred to form a homogeneous solution. The solution was placed in brown glass bottles to prepare an oral aqueous preparations of 1α-hydroxycholecalciferol (Example 3).

At the same time, sodium D-tartarate was used instead of trisodium citrate dihydrate in Example 3 to prepare another oral aqueous preparation (Example 4), and butylhydroxytoluene was used instead of tocopherol in Example 3 to prepare the third oral aqueous preparation (Example 5).

At the same time, the fourth oral aqueous solution containing disodium edetate instead of trisodium citrate dihydrate in Example 3 was prepared as a comparison (comparison 4) and the fifth oral aqueous preparation containing lysine instead of trisodium citrate dihydrate in Example 3 was prepared as another comparison (Comparison 5), too.

These oral aqueous preparations (Examples 3 through 5 and Comparisons 4 and 5) were stored at room temperature to examine the residual rate of 1α-hydroxycholecalciferol, the principal ingredient of the preparations. The results are shown in Table 5.

TABLE 5

Stability of oral aqueous preparations

| Preparations | Storage conditions room temperature | | | |
|---|---|---|---|---|
| | 1 Mon. | 3 Mon. | 6 Mon. | 12 Mon. |
| Example 3 | 96 | 95 | 96 | 94 |
| Example 4 | 97 | 97 | 94 | 95 |
| Example 5 | 95 | 95 | 93 | 94 |
| Comparison 4 | 95 | 89 | 80 | 63 |
| Comparison 5 | 97 | 91 | 83 | 81 |

We claim:

1. An aqueous preparation of active form of vitamin $D_3$, comprising the active form of Vitamin $D_3$, a nonionic surface active agent, an antioxidant and at least one chelating agent selected from the group consisting of citric acid, tartaric acid and metal salts thereof,
   wherein the active form of Vitamin $D_3$ is (i) solubilized with the nonionic surface active agent and (ii) stabilized with a combination of the antioxidant and the at least one chelating agent,
   wherein the amount of said at least one chelating agent is 100 to 10,000 parts by weight per 1 part by weight of the active form of Vitamin $D_3$, and
   wherein the active form of vitamin $D_3$ is at least one selected from the group consisting of 1α,24-dihydroxycholecalciferol, 1α-hydroxycholecalciferol, 1α,25-dihydroxycholecalciferol, and 1α,25-dihydroxycholecalciferol-26,23-lactone.

2. The aqueous preparation of claim 1, wherein the chelating agent is sodium citrate or sodium tartarate.

3. The aqueous preparation of claim 1, wherein said antioxidant is at least one selected from the group consisting of metal salts of ascorbic acid, tocopherol, butylhydroxytoluene, butylhydroxyanisole, propyl gallate, and nordihydroguaiaretic acid.

4. The aqueous preparation of claim 3, wherein the amount of said antioxidant is 500 to 20,000 parts by weight per 1 part by weight of the active form of vitamin $D_3$.

5. The aqueous preparation of claim 1, wherein said nonionic surface active agent is polyoxyethylene hardened castor oil derivative or polyoxyethylene sorbitan fatty acid ester.

6. The aqueous preparation of claim 5, wherein the amount of said nonionic surface active agent is 300 to 500,000 parts by weight per 1 part by weight of the active form of vitamin $D_3$.

7. A method for preparing a stabilized aqueous preparation of active form of vitamin $D_3$ comprising the steps of: preparing a thick solution of the active form of vitamin $D_3$ in a nonionic surface active agent and adding said thick solution to an aqueous solution containing a combination of at least one chelating agent selected from the group consisting of citric acid, tartaric acid and metal salts and an antioxidant.

* * * * *